United States Patent [19]

Cazer et al.

[11] Patent Number: 5,071,547

[45] Date of Patent: Dec. 10, 1991

[54] COLUMN CHROMATOGRAPHIC COLUMN APPARATUS WITH SWITCHING CAPABILITY

[75] Inventors: Frederick D. Cazer, Earlville; Barry L. Scott, Norwich; Garth E. Strobel, Smyrna, all of N.Y.

[73] Assignee: Separations Technology, Inc., Wakefield, R.I.

[21] Appl. No.: 498,112

[22] Filed: Mar. 23, 1990

[51] Int. Cl.⁵ .............................................. B01D 15/08
[52] U.S. Cl. ................................ 210/198.2; 210/96.1; 210/659; 55/386
[58] Field of Search ............... 210/635, 656, 659, 96.1, 210/143, 198.2; 55/386

[56] References Cited

U.S. PATENT DOCUMENTS

| | | | |
|---|---|---|---|
| 3,373,872 | 3/1968 | Hrdina | 210/198 |
| 3,508,880 | 4/1970 | Hrdina | 23/253 |
| 3,686,117 | 8/1972 | Lauer et al. | 210/31 C |
| 3,923,460 | 12/1975 | Parrott et al. | 23/210 R |
| 4,102,179 | 7/1978 | Snell | 73/61.1 C |
| 4,154,583 | 5/1979 | Favre | 210/198.2 |
| 4,158,630 | 6/1979 | Stearns | 210/198.2 |
| 4,204,952 | 5/1980 | Snyder | 210/31 C |
| 4,271,697 | 6/1981 | Mowery, Jr. | 73/61.1 C |
| 4,274,967 | 6/1981 | Snyder | 210/659 |
| 4,366,060 | 12/1982 | Leiser | 210/198.2 |
| 4,412,866 | 11/1983 | Schoenrock | 210/656 |
| 4,454,043 | 6/1984 | Ting et al. | 210/659 |
| 4,544,485 | 10/1985 | Pinkerton et al. | 210/502.1 |
| 4,577,492 | 3/1986 | Holba | 210/198.2 |
| 4,724,081 | 2/1988 | Kawahara et al. | 210/659 |
| 4,751,185 | 6/1988 | Ono et al. | 436/24 |
| 4,913,821 | 4/1990 | Melcher | 210/198.2 |

OTHER PUBLICATIONS

"Increased Sample Throughput in HPLC Using Sample Switching", Chromatographia, vol. 19 (1984) by C. J. Little and O. Stahel, pp. 322–326.
"Column Switching Techniques in Modern HPLC", American Laboratory, vol. 16, No. 10, Oct. 1984, pp. 120-129.
"Advantages of Pre-Column and Multicolumn Switching and Preparative HPLC", American Laboratory, by George D. Mack, vol. 19, No. 12a, Dec. 1987.
"Precolumn Concentration and/or Stepwise-Gradient Elution by Switching Valve Techniques in Micro High--Performance Liquid Chromatography", Journal of Chromatography, 407 (1987), pp. 141–150.
"Liquid Chromatography in Environmental Analysis", ed. James F. Lawrence for Health and Welfare Canada, Human Press, N.J., pp. 303-338, 1979.

Primary Examiner—Ernest G. Therkorn
Attorney, Agent, or Firm—Donald Brown; Peter F. Corless

[57] ABSTRACT

The present invention involves a dual column chromatographic apparatus with column switching capability that is useful in any pressurized fluid chromatography system. The apparatus has at least a first and second chromatographic column, a detector, a fluid conveyance system having a multivalve arrangement, pressurizable fluid conduit assembly, and a controller.

The columns are adapted for containing stationary phase or packing for separation of a multicomponent sample into one or more components. The multi-valve arrangement has a plurality of multi-port, multi-modal valves and can include an ingress-egress valve; a guard pre-column valve; detector isolation valve; a set of four, four-port, multi-modal valves; or a set of two four-port, multi-modal valves and one six-port, multi-modal valve or a first valve set and a second valve set. The two chromatographic columns, multi-valve arrangement, and detector are linked for pressurized fluid communication by the pressurized fluid conduit assembly. This conduit assembly with pressurization enables the passage of the fluid mobile phase with or without a sample into the multivalve arrangement, between the valves of the multi-valve arrangement, from and to the multi-valve arrangement and the first column, from and to the multi-valve arrangement and the detector, from and to the multi-valve arrangement and the second column, and out of the multi-valve arrangement. An electronic, pneumatic, or hydraulic controller is connected for actuating action with the valves in the multi-valve arrangement to change one or more of the valves from one state of pathways to another state of pathways.

28 Claims, 3 Drawing Sheets

COLUMN CHROMATOGRAPHIC COLUMN APPARATUS WITH SWITCHING CAPABILITY A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The present invention is directed to an apparatus and method for pressurized fluid chromatography. More particularly, the present invention is directed to an apparatus and method for accomplishing myriad functions in a dual column pressurized fluid chromatography apparatus.

Pressurized fluid chromatography, especially liquid chromatography usually referred to as high performance liquid chromatography (HPLC) has been conducted with one or more columns. Also, the technique of column switching has been utilized in the art to separate a sample on a system of columns, where the columns have a similar or different stationary phase. Another technique used in chromatographic columns is the backflushing of a single column. An example of column switching involves injection of the sample onto an column, elution of the peaks of interest, and backflushing of the column. The backflushing technique is commonly used to remove from the column material that is strongly retained on the column. The expansion of use of the column switching techniques resulted from development of switching valves that operate under pressures up to 7,000 psi (48.3 megapascals) for thousands of switching operations. The switching valves also must operate without significantly broadening the peaks of the solute and the mobile phase. This is accomplished by utilizing switching valves that have a very low hold-up volume.

Column switching is embraced by the art to accomplish various separate techniques such as: enrichment of trace materials, recycling of materials to enhance the peaks, column clean-up or regeneration, and zone cutting to increase throughput.

A difficult task that exists in the field of pressurized fluid chromatography is adequately separating overlapping peaks produced from multi-constituent materials when the materials are analyzed or when they are separated on a preparative scale through chromatography. This is especially true in the area of preparative as opposed to the analytical.

It is an object of the present invention to provide a chromatographic apparatus and method useful in separating overlapping peaks in the chromatography generated from materials being separated where the apparatus and method are applicable to preparative.

SUMMARY OF THE INVENTION

The foregoing objects and other objects gleaned from the following disclosure are accomplished by the present invention.

One aspect of the present invention is a dual chromatographic column apparatus with column switching capability that is useful in pressurized fluid chromatographic systems. This apparatus has at least two chromatographic columns; at least one detector; a fluid conveyance system, having a multi-valve arrangement; a fluid conduit assembly; and controller for the fluid conveyanca system. The chromatographic columns, detector, multi-valve arrangement, and conduit assembly are adapted for pressurized fluid chromatography. The columns are adapted for containing stationary phase or packing for separation of one or more constituents from a multi-constituent sample (hereinafter referred to in this disclosure as "Sample"). The multi-valve arrangement in one aspect of the invention has a plurality of multi-port and multi-modal valves, and in another aspect has two sets of more than one multi-port and multi-modal valve. The multi-valve arrangement in conjunction with the fluid conduit assambly and controller can accomplish various functions. These include the passage of mobile fluid phase with or without sample into the dual chromatographic column apparatus rather than by-passing this apparatus and for a forward flow mode and for backflushing mode flow through the apparatus. In the forward flow mode the apparatus has the capability for: selection of at least one column for flow with the detector, re-direction of the flow to the other column in at least one direction after passage through the detector, and recycling back through one or more columns. In a backflushing flow mode the apparatus has the capability for backflushing with mobile phase for at least both columns sequentially.

In the multi-valve arrangement, each valve is adapted for actuation so each valve is capable of changing to its additional modes or states via signals to and from the controller. The plurality of valves in the arrangement include an ingress-egress valve, and a sufficient number of multi-port and multi-modal valves in a effective relationship to each other to convey pumped fluid mobile phase with or without sample: to either the first or second or to both columns in any consecutive ordar, and to the detector after each or several passes through one or more columns in at least a forward flow mode. The ingress-egress valve provides the pumped fluid mobile phase with or without Sample to the apparatus in a forward flow mode or the mobile phase in a backflushing or backwashing mode. Also this valve provides for exit from the apparatus of the mobile phase with or without Sample or separated constituents thereof for collection or to waste.

In one embodiment of this effective relationship the multi-valve arrangement has two sets of valves, the first and second set interact with each other to provide the forward flow and backflushing modes. The first set can include the ingress-egress valve or that valve can stand alone before, for forward flow, or after, for backflushing, the first set. The first set in a forward flow mode provides for delivery to either or both columns, consecutively, and for receipt of the mobile phase with or without the Sample from either or both of two pathways from the second valve set, and can route the mobile phase with or without the Sample from one or both of these pathways to the ingress-egress valve. In a backflushing mode the first set receives the fluid mobile phase from either or both, consecutively, of the columns. Also in this mode the first valve set communicates with the second valve set via the same pathways but with the opposite direction of flow in each, and delivers to rather than receives from the ingress-egress valve for delivery to collection or waste. The second valve set in a forward flow mode: receives the output effluent from one or both of the chromatographic columns, provides for delivery of these effluents at appropriate times to the detector, receives the effluent from the detector, routes the effluent of one column to the other column through one pathway with the first valve set, and communicates with the first valve set via another pathway for disposition of the mobile phase with or without Sample or constituents thereof to the ingress-egress valve for collection. The ingress-egress valve, two chromatographic columns, first and second valve sets and detector are linked for pressurized fluid communication by the pressurizable fluid conduit assembly.

The fluid conduit assembly with pressurization conducts the pumped fluid mobile phase with or without a Sample into and between the valves of the multi-valve arrangement, the two chromatographic columns and the detector as follows: into the multivalve arrangement, from and to the multi-valve arrangement and the first column, from and to the multi-valve arrangement and the detector, from and to the multi-valve arrangement and the second column, and out of the multi-valve arrangement and between the valves in the multi-valve arrangement to accomplish the following flow pathways. The forward flow pathways are at least the following: bypass, first column to detector, second column to detector, first column to detector to second column and second column to detector to first column. The backflush pathways are at least: to the second column, to the first column.

The controller communicates with the actuator of each valve of the multi-valve arrangement to be capable of at least transmitting a signal to sctuate one or more valves. The actuation causes the valve to change its or their state of routing in order to establish at least the (i) pressurized fluid communication for mobile phase with or without sample into the multi-valve arrangement, (ii) sequence of column selection and redirection in the forward flow and backflush modes to provide for the configuration changes to the dual column apparatus, and (iii) pressurized fluid communication for at least mobile phase with or without Sample or constituents of the Sample for collection or for waste. The communication is by electronic means, pneumatic means, or hydraulic means.

The apparatus finds utility in pressurized fluid chromatographic systems such as those with at least one mobile phase reservoir and at least one pump, both of which communicate with the pressurizable fluid conduit assembly. Also, the system has a Sample injector that communicates with the dual column apparatus so that one or more samples can be combined with the fluid mobile phase and passed to the ingress-egress valve to enter the dual column apparatus.

Another aspect of the present invention is a method of separating overlapping peaks which involves passing the fluid mobile phase with Sample to a first column to a detector, to a second column to a detector and subsequently to both columns with sequential passes to a detector. More particularly the method involves: eluting a Sample onto a first column, resolving a quickly eluting impurity peak, collecting the eluant, collecting a small fraction of the first peak of the two peaks of interest starting to elute from the first column, changing the column configuration from column 1 to the detector to collection to that of column 1 through the detector to column 2, switching the column configuration after the two peaks of interest have completely eluted onto column 2 so that column 1 can be backflushed to remove slowly eluting contaminants, reequilibrating column 1 with mobile phase, switching the column configuration to elute the materials of interest from column 2 through the detector to collection, collecting another small fraction of the first component as the peak begins to elute from column 2, switching the column configuration from column 2 to the detector to collection to that of column 2 through the detector to column 1, collecting a trailing fraction of the second component eluting from column 2 as the last of the Sample constituents elutes from column 2, changing the column configuration to allow for backflushing and reequilibration of column 2, elute the materials of interest through both columns 1 and 2 through the detector, collect the product-bearing fractions, change the column configuration so that columns 1 and 2 can be backflushed individually or simultaneously, and switch the column configuration to system bypass. This simultaneous backflushing occurs with the detector isolated out of the system.

Optionally and preferably a guard column is present in the apparatus and method of the present invention by linking it with the pressurizable fluid conduit assembly between the ingress-egress valve and the next multiport and multi-modal valve in the multi-valve arrangement or in the first valve set. This linkage is through a valve allowing for bypass of the guard column and for passage of the fluid under pressure to and from the guard column. The guard column can have a stationary phase which is similar to or different from that of the chromatographic columns. Through this described linkage fluid mobile phase with or without Sample enters a loop from the ingress-egress valve to the precolumn valve to the precolumn and the passage of eluant from the precolumn to the precolumn valve for conveyance to the next multi-port and multi-modal valve or first valve set. This passage and conveyance occurs as that part of the loop acting as a component part of the fluid conduit assembly.

In the method of the present invention the first switching of the column configuration from system bypass allows the mobile phase to enter the precolumn and the first and second chromatographic columns to equilibrate the supports or stationary phases in all of the columns After equilibration the Sample is again injected and the Sample is eluted through the precolumn and onto the first chromatographic column. At this point the precolumn can be switched out of the apparatus, and the process can be conducted with no precolumn in the apparatus. After the product bearing fractions are collected, the precolumn and the first and second chromatographic columns can be backflushed individually or simultaneously. Also it is optional, but preferable, to have present at least one multi-port and multi-modal valve isolating the detector from the pressure of the apparatus and providing two-way flow, forward and backflush, so that in backflushing the detector can be by-passed.

DETAILED DESCRIPTION OF THE INVENTION

Figure 1:
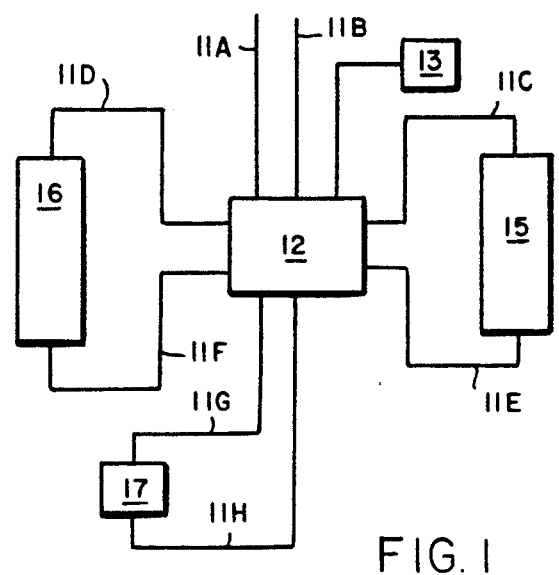
FIG. 1 is a schematic diagram of the dual column switching chromatographic apparatus for use in pressurized fluid chromatographic systems, wherein the apparatus has two columns, detector, and a fluid conveyance system comprised of multi-valve arrangement, fluid conduit assembly, and controller.

To separate overlapping chromatographic peaks on a preparative scale requires numerous capabilities of a system. Enrichment, zone cutting and recycle along with backflushing can be used to accomplish improved peak distinction of overlapping peaks. Even with pressurized fluid chromatographic separations of the more easily separated samples, the techniques of recycle and backflushing and the like are useful. Recycle allows the use of additional shorter columns rather than fewer longer columns. This is a benefit in regards to column packing and reducing back pressure Shorter columns are easier to pack with the stationary phases and they build up less back pressure, whereas the longer the column the more difficult it is to pack and there is an increase in back pressure. Also it is advantageous in a pressurized fluid chromatographic system to use the fewest possible pumps and detectors. The present invention permits one to take advantage of these possibilities.

FIGS. 1-5 depict the dual column switching apparatus in various embodiments using in many or most of the Figures: chromatographic columns, a detector, valves, pressurizable conduit and a controller. Generally all of these devices are those that are known to those in the field of pressurized fluid chromatography. Hereinafter for convenience of referring to the at least dual chromatographic column apparatus it will be referred to as "DCC Apparatus".

Nonexclusive examples of chromatographic columns include micro and macrobore columns, U-shaped and coiled columns and the like. Packings otherwise referred to as the stationary phase can be any of the microporous particles or porous layer beads (pellicular beads) known to those skilled in the art to be suitable for particular samples or constituents of samples. A nonexclusive example of a suitable column is that disclosed in U.S. Pat. No. 4,582,608, which patent is hereby incorporated by reference. A nonexclusive example of useful stationary phases includes silica based media of either bonded or straight phase available from a number of manufacturers known to those skilled in the art, where one such manufacturer is YMC, Inc., Cedar Grove, N.J.

Nonexclusive examples of detectors include the full flow cell type of detector like the ultraviolet light or radiation absorption detectors and the refractive index detectors and the conventional types of ultraviolet absorption, photometers, differential refractometers, fluorophotometers, flame ionization detectors, infrared absorption photometers, polarographs, electric conductivity detectors, thermal conductivity detectors and radioactivity counters and the like. The full flow cell detector is preferred but the conventional detectors are useful with proper isolation of the detector from the pressure of the DCC Apparatus. An intermediate valve or bleed streams to and from the detector provide suitable isolation, although the latter can reduce the flow by around 10 percent.

The valves of the multi-valve arrangement in the fluid conveyance system are any multi-port and multi-modal valves with actuators capable of operation under superatmospheric pressures known in pressurized fluid chromatography. The valves can have four or more ports including six, eight and ten port valves, and can be multi-modal to have two or more channels or flowpaths for routing fluid. The multi-modal characteristic involves changing the state of the valve from the unactuated state, where the valve provides for at least two channels of flow or routing, to the actuated state, where the valve provides for two different channels of flow. Even though the channels are provided, they need not necessarily be used in all of the configurations of the DCG Apparatus. The state of the valve is changed through the valve's actuator in conjunction with a controller. The actuator is a pneumatic, electronic or hydraulic valve diverter or positioner The ingress-egress valve is preferably a multi-port and multi-modal valve, but it may be a set of two simple valves, one to divert flow from one direction to a direction for conveyance into the apparatus and another valve to prevent back flow into the DCC Apparatus from collection or waste. Also anytime a valve is a four-port valve it can be replaced by a set of two three-port valves, where one port of each valve provides for connection to the other three-port valve. For example, the valves can be any 4-port, bimodal valves appropriate for use with pressurized fluid chromatography. Such valves are known to those skilled in the art and a nonexclusive example of such a valve is that available under the trade designation, Whitey Valves, available from Whitey Corp., Highland Heights, Ohio 94143.

The controller can be a separate controller means or a part of a controller or controller means for the pressurized fluid chromatographic system. By part of a controller, it is meant that the controller can control more than the DCC Apparatus and could control the entire pressurized fluid chromatographic system (PFCS) including, without limitation, at least one pump, differential fluid mobile phase mixing and utilization, Sample injection, conveyance of fluid in the PFCS, pressurization of the PFCS and display of the results of the chromatographic separations and storage of the results for recall at a later time. The controller is associated with means for generating and transmitting to the actuator of each valve in the multi-valve arrangement a process directive signal upon receipt of a process signal and/or manually entered external signals or upon generation of a controller process signal. Such a controller can be any open or closed loop controller for on-off or proportional action. For a pneumatic controller, compressed air is supplied to a controller and the actuators of the valves. The controller can have a flapper-nozzle mechanism to provide the means of controlling the pneumatic output. When the flapper is moved away from the nozzle of the compressed air supply to the controller an air control relay sends a maximum signal to the actuator to cause the valve to change its state. When the flapper is moved against the nozzle, a minimum signal is sent to the actuator which reverts to its unactuated state. An electronic on-off control action is achievable by any device known to those skilled in art that opens or closes an electrical circuit to actuate the actuator of a particular valve; for example, switches. Associated with these control devices the controller would also include an initiating device such as a programmer, programmable sequencer or microprocessor, a programmable microcomputer or personal computer or mini-computer having particular programs for control of the DCC Apparatus. A programmer could be operated on a time cycle or by other means and the programmer could by replaced by a human being. When the controller is part of the PFCS controller the personal or mini computer can have programs, or can have routines or subroutines of a larger program for controlling the DCC Apparatus in addition to programs or in addition to routines or subroutines of a larger program for controlling other functions or actions of the PFCS. For a total electronIc controIIer the controller would also have signal transmitting, generating, storing and handling means provided by electrical switches, relays, wiring and the like known to those skilled in the art.

The fluid conduit assembly is any pressurizable conduit known to those skilled in the art to handle the pressures of gas or pressurized liquid chromatography including high performance liquid chromatography. The fluid conduit assembly in conjunction with the multi-valve arrangement provides for communication to a collection or waste station or reservoir and minimal, if any, flow blockages through the DCC Apparatus to avoid any dangerous build up of pressura in the DCC Apparatus.

FIG. 1 sh6ws a DCC Apparatus useful in PFCS having two chromatographic columns, detector, and fluid conveyance system comprised of: multi-valve arrangement, fluid conduit assembly, and controller. This DCC Apparatus communicates with the PFCS by two conduits, 11A and 11B, of the fluid conduit assembly. The fluid conduit assembly, generally indicated as, 11, is the assembly of all the pressurizable conduits to convey fluid into, in, and out of the DCC Apparatus One of the conduits of 11A or 11B delivers at an elevated pressure the fluid mobile phase with or without the multiconstituent Sample to the DCC Apparatus As delivered to the DCC Apparatus, the superatmospheric pressure, mobile phase constitution, and Sample injection have been prepared from other parts of the PFCS. The other conduit of 11A or 11B carries the fluid mobile phase without the multiconstituent Sample or with separated constituents of the Sample for waste, recycle and/or collection In this aspect of the invention the multi-valve arrangement, 12, receives the fluid at the elevated pressures known to those skilled in the art for PFCS and in conjunction with Controller, 13, determines whether the flow through the DGC Apparatus is forward flow or backflush flow. Controller 13 and multi- valve arrangement 12 interact as described above through actuators (not shown in FIG. 1) for each of the valves (not shown in FIG. 1) comprising the multi-valve arrangement 12 through connection 14. This connection can be electronic, pneumatic or hydraulic for connection and actuation of the more than one valve of the multi-valve arrangement 12.

Figure 5:
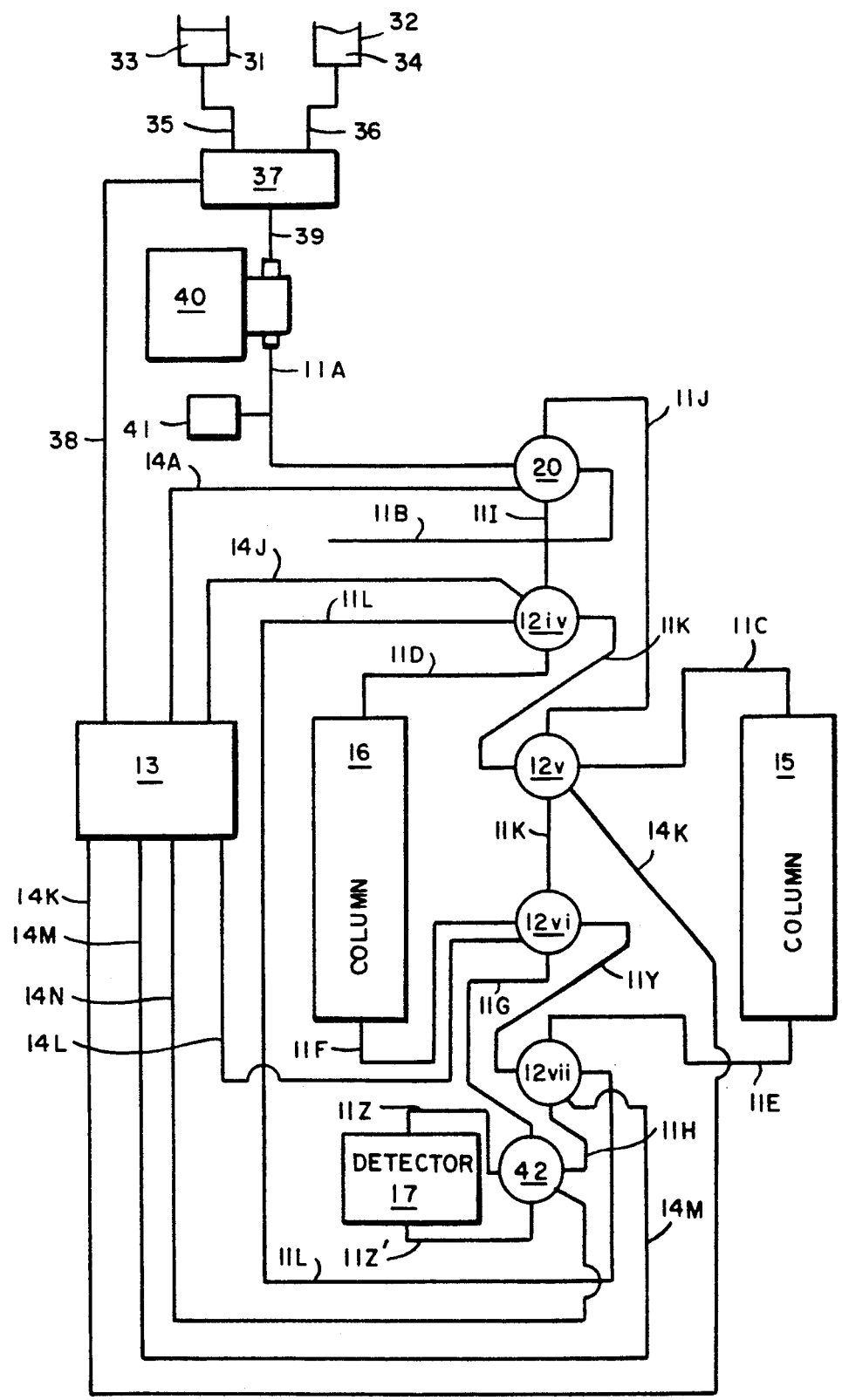
FIG. 5 is a schematic of a high performance chromatographic system with the dual column switching apparatus as part of the system.

Multi-valve arrangement 12 in the forward flow mode delivers the fluid mobile phase with or without the Sample to one or the other of the chromatographic columns, 15 or 16, through conduits 11C and 11D, respectively, of the fluid conduit assembly 11. The fluid mobile phase with or without Sample elutes through one or the other of columns, providing for some degree of separation of some of the constituents of the Sample when the Sample is present. Eluting effluent from columns 15 and 16 pass through conduits 11E and 11F, respectively, of the fluid conduit assembly 11 to the multi-valve arrangement 12. Arrangement 12 either re-directs the effluent to the other column through conduits 11C or 11D or to detector 17 before passage to another column or without passage to another column. Passage to and from the detector 17 occurs through one or the other of conduits 11G and 11H. These conduits can be bleed streams, as they are shown in FIG. 5 as conduits 11z and 11z', if the detector is not a full cell type of detector; otherwise these conduits can be similar to the other conduits of the fluid conduit assembly 11.

In the backflush mode of operation, multi-valve arrangement 12 receives mobile phase with a particular constitution from either conduit 11A or 11B from the PFCS, and arrangement 12 delivers fluid mobile phase by conduits 11E or 11F to columns 15 and 16, respectively. The mobile phase leaves the columns 15 and 16 by conduits 11C and 11D, respectively, for passage to multi-valve arrangement 12. Arrangement 12 directs the mobil phase to exit, when only one column is backflushed or redirects the mobile phase to the other column, when both columns are backflushed in consecutive fashion. The detector 17 can also be flushed with mobile phase, when a check valve such as valve 42 in FIG. 5 is present and is in the proper configuration. The flushing is preferably performed in the forward flow mode of flow operation, and is limited to forward flow if a bleed line or directional check valve is present in the detector loop. Exit from the DCC Apparatus in the backflush mode can be through the same conduit 11A or 11B as is the exit for the forward flow mode, where the multi-valve arrangement 12 directs the flow to the proper conduit for exit in both modes of flow. Upon exiting from the DCC Apparatus the fluid, depending on whether it is fluid mobile phaae or constituents of the Sample and mobile phase, pass to waste or recycle, or collection or waste in other parts of the PFCS. The latter determination is made depending on desired application such as if the PFCS is operated on an analytical scale or a preparative scale.

Figures 2, 4:
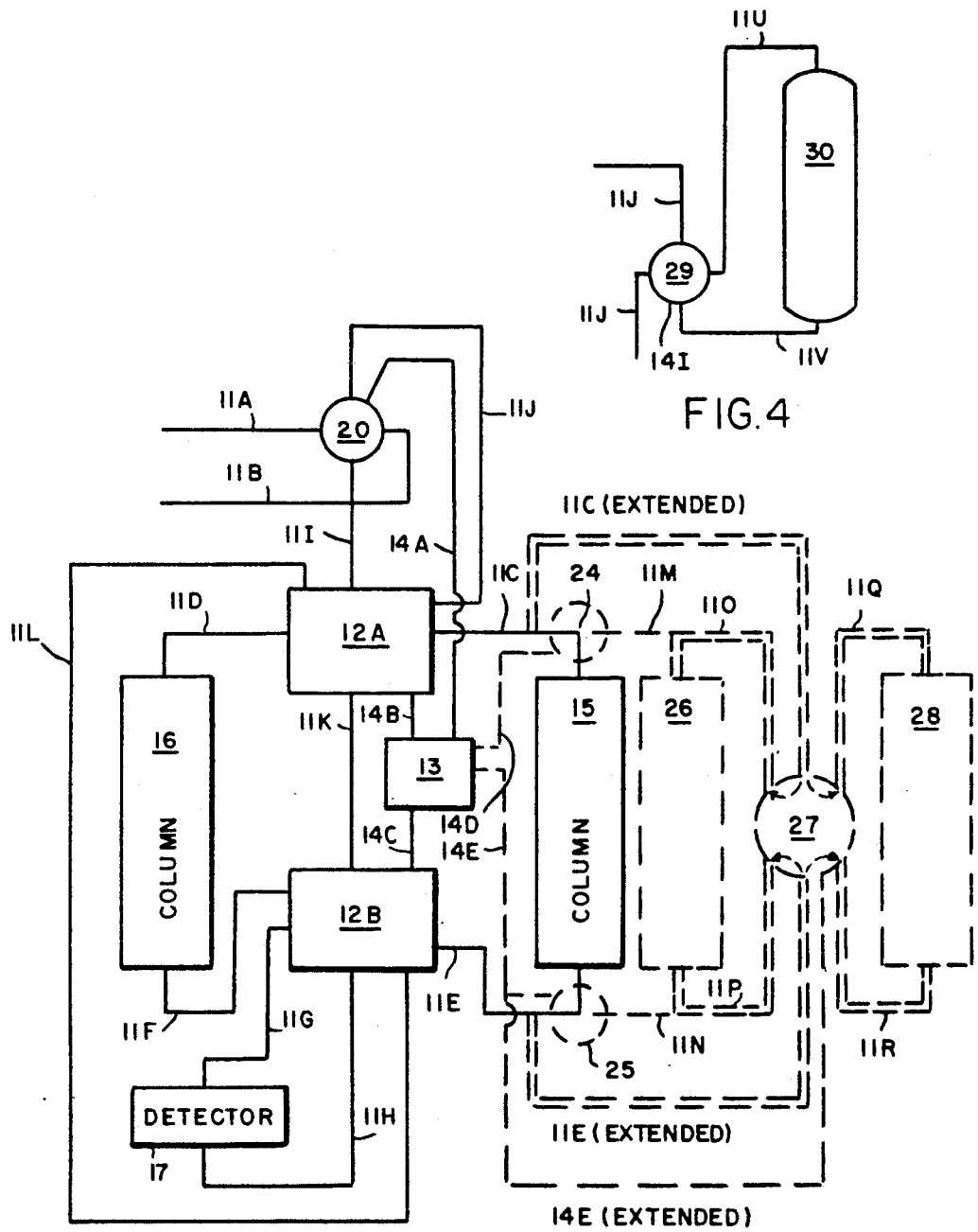
FIG. 2 is a schematic diagram of the dual column switching chromatographic apparatus similar to that of FIG. 1, except that the multi-valve arrangement has an ingress-egress valve and two sets of more than one multi-port and multi-modal valve and the figure shows in phantom the connection of additional columns along with two types of valve connections for these additional columns to associate with the dual column switching apparatus.
FIG. 4 is a schematic diagram of the precolumn and precolumn valve for connection to the dual column switching apparatus.

FIG. 2 depicts the DCC Apparatus with several of the valves of the multi-valve arrangement 12A and 12B and with optional additional chromatographic columns shown in two alternative modes of connection. In the description of FIG. 2 those features that are similar to the features of FIG. 1 will be described with the same reference number to provide consistency and a further and fuller understanding of the invention. As in FIG. 1 the constitution of the fluid mobile phase with or without Sample is determined in another part of the PFCS. The phase with or without Sample enters the DCC Apparatus through conduit 11A or 11B, one of which serves as an inlet and the other as an outlet to and from the DCC Apparatus Conduits 11A and 11B are part of the fluid conduit assembly 11 and are connected for pressurized fluid flow with an ingress-egress valve 20. This valve is part of the multi-valve arrangement 12 of FIG. 1 or can stand alone outside the arrangement as shown in FIG. 2 although in FIG. 2 valve 20 can still be part of the multi-valve arrangement.

As in FIG. 1 this ingress-egress valve allows for the mobile phase alone or with the Sample to move into the DCC Apparatus by the pressurizable fluid conduit assembly, 11, in this section of the assembly of 11A or 11B and to receive the resultant effluent from the DCC Apparatus through the fluid conduit assembly here at 11I or 11J.

In FIG. 2 the multi-valve arrangement is comprised of two valve sets, 12A and 12B, where each set has more than one multi-port and multi-modal valve. Valve set 12A receives the mobile phase with or without the Sample in the fluid conveyance system through the fluid conduit assembly, 11, by passage through valve 20 and conduit 11J. Valve 20 in conjunction with valve set 12A allows for bypass of the apparatus through conduits 11A, 11B, 11J, and 11I. The valve set can be one valve or a plurality of valves having the appropriate ports to allow for the following conveyances. A port for entry of the mobile phase with or without Sample, a port for ingress or egress from a first column, 15 in FIG. 2; two separate ports for fluid communication by two separate pathways with valve set 12B; a port for ingress or egress to the second column of the dual column chromatographic apparatus referred to in FIG. 2 as numeral 16; and an egress path to the ingress-egress valve 20.

The fluid conduit assembly provides conduits for pressurized fluid communication with the ingress-egress valve, columns, valve arrangement, and detector. Conduits 11C and 11E provide communication between valve set 12A and column 15 and column 15 and valve set 12B. In the forward flow mode conduit 11C delivers to and conduit 11E removes from column 15, while in the backflush mode it is just the reverse. Valve set 12B is at least one or a plurality of valves with the capability of allowing ingress and egress from column 15; column 16; and the detector 17 and two pathways for ingress and egress for valve set 12A. Conduits 11K and 11L of the fluid conduit assembly link the valve sets 12A and 12B for the two separate pathways of fluid communication. Also, the fluid conduit assembly has conduits 11G and 11H which link for fluid conveyance the valve set 12B and the detector 17. As mentioned for FIG. 1 the flow path through the detector 17 should be in one direction for forward flow and for rinsing or washing. Conduit 11D of the fluid conduit assembly links the first valve set 12A to column 16 for ingress of mobile phase with or without Sample in the forward flow path and for egress of mobile phase in the backflush flow path. Valve set 12A ties in with the ingress-egress valve 20 through conduit 11I of the fluid conduit assembly. Conduit 11F receives the effluent from column 16 in a forward flow mode and delivers mobile phase in the backflush mode. Conduit 11F connects column 16 with valve set 12B. The fluid conduit assembly is comprised of conduits 11A through and including 11L which transport the mobile phase with or without Sample or separated samples to and from the columns and/or detectors and also allows for backflushing of the columns and dual chromatographic column apparatus.

The controller 13 is connected to the actuators of valve 20 through actuating connection 14A and the valves in valve set 12A through connection 14B and to those of valve set 12B through connection 14C. Controller 13 through these connections actuate one or more of the valves in those valve sets to reconfigure the DCC Apparatus for different flow in either the forward or backflush modes to accomplish the desired configurations.

The dual column switching valve apparatus of FIG. 2 can provide the following column configurations: a) forward flow: system bypass, column 15 to detector 17, column 16 to detector 17, column 15 to column 16 to detector 17, column 16 to column 15 to detector 17, column 15 to detector 17 to column 16, column 16 to detector 17 to column 15; and b) backflush: column 15, column 16, column 16 to column 15, column 15 to column 16, detector 17 to column 16, detector 17 to column 15 to column 16, and detector 17 to column 16 to column 15 The outlet from the dual chromatographic column apparatus to the ingress-egress valve, 20, is through conduit 11I in forward flow and through 11J in backflush flow.

Also shown in FIG. 2, in phantom, is the presence of one or two additional chromatographic columns with two alternative approaches to connection. Although FIG. 2 shows the additional columns on one side of the DCC Apparatus, any additional columns can be on either or both sides of the DCC Apparatus with appropriate connections as shown in FIG. 2

One approach to connecting additional columns that is shown in FIG. 2 has a multi-port, multi-modal valve, 24, on conduit 11C. This valve connects for pressurized fluid delivery to either column 15 or conduit 11M for either a forward flow or a backflush mode. At the other end of the column, here column 15, there is located another multi-port and multi-modal valve, valve 25. This valve receives the effluent from or delivers mobile phase in a backflush mode to column 15. Also the valves 24 and 25 connect column 26 to the DCC Apparatus through conduits 11M and 11N of the fluid conduit assembly, 11. The controller 13 connects to the actuators of valves 24 and 25 through connections 14D and 14E, respectfully. With this arrangement, controller 13 can signal a switch of the valve to route fluid mobile phase with or without Sample or constituents thereof to column 15 or to conduit 11M for delivery to a third chromatographic column, 26. Also controller 13 can signal a concomitant switch of valve 25 for effluent to pass from column 26. The configurations that are possible with this arrangement include recycling and redirecting to column 26 for equilibration or re-packing or the like to column 15.

Another connection approach for one or more additional chromatographic columns involves that depicted in FIG. 2 by the double phantom lines. In this arrangement column 26 replaces column 15, which would not be present in the DCC Apparatus, and valves 24 and 25 and conduits 11M and 11N indicated by single phantom lines would ba absent Conduits 11C and 11E would extend to include the double phantom lines and would connect for pressurized fluid flow with the six-way valve, valve 27. Here conduits 11C and 11E are directly connected to valve 27 rather than column 15. Controller 13 is connected for actuation of the valve through connection 14E (extended) or 14D (extended) to the actuator of valve 27 to switch connection for pressurized fluid flow to either column 26 or another chromatographic column, column 28. These connections for fluid flow are through the fluid conduit assembly's conduits 11O and 11P for column 26 and conduits 11Q and 11R for column 28. Either conduit 11O or 11Q can deliver in a forward flow mode to or receive in a backflush mode from columns 26 and 28, respectively. Likewise conduits 11P or 11R receive in a forward flow mode from and deliver in a backflush mode to columns 26 or 28, respectfully. Valve 27 is connected for pressurized fluid flow by conduit 11E (extended) to valve set 12B and by conduit 11C (extended) to valve set 12A.

Figure 3:
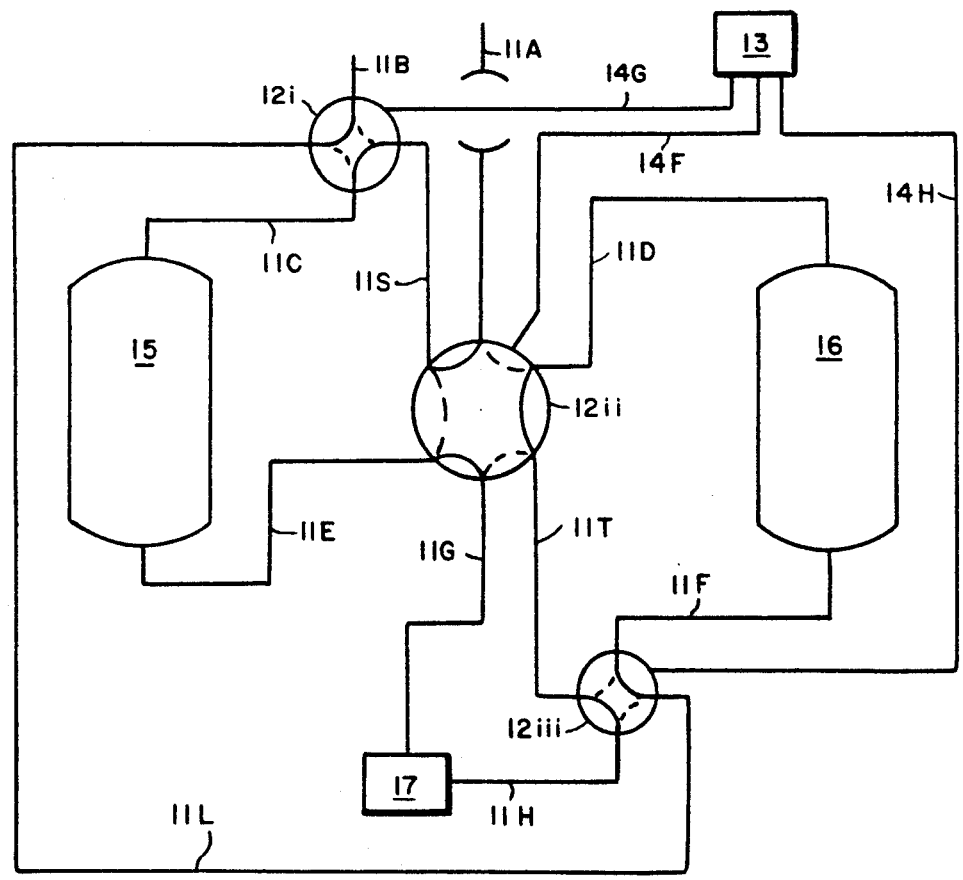
FIG. 3 is a schematic diagram of the dual column switching chromatographic apparatus showing a multi-valve arrangement comprising two four-port and multi-modal valves and one six-port and multi-modal valve and their connections to the columns and the detector and their part in the fluid conveyance system.

As in FIGS. 1 and 2, FIG. 3 uses similar reference numbers for similar components of the DCC Apparatus. As in FIG. 2, FIG. 3 has a first column, 15; and a second column, 16; detector, 17; and a controller, 13; and a fluid conduit assembly having conduits; 11A through 11H and 11L, 11S, and 11T; a multi-valve arrangement, 12; and actuating connections 14F through 14H to connect the controller 13 to the multi-valve arrangement. All of these components of the DCC Apparatus, except for the multi-valve arrangement, have the same functions as those explained for similarly referenced components of FIGS. 1 and 2 The multi-valve arrangement 12 has similar functions to that of FIGS. 1 and 2 given its particular configuration of: one four-port, multi-modal valve, 12$i$; one six-port, multi-modal valve, 12$ii$; and another four-port, multi-modal valve, 12$iii$. Conduit 11A is connected for pressurized fluid flow, as are all of the connections for the DCC Apparatus shown in FIG. 3, to one port of valve 12$ii$. This valve in one of its states, actuated or unactuated, is connected through another of its ports to one of the ports of valve 12$i$ or through another of its ports to column 16. The latter connection is through conduit 11D, and the former connection is through conduit 11S, which is a conduit of the fluid conduit assembly. The three ports of valve 12$ii$ and the valve 12$i$ conceptually constitute the first valve set 12A of FIG. 2. Valve 12$i$ in one of its states, actuated or unactuated, is connected through another of its ports by conduit 11C to column 15. Also in this state valve 12$i$ at another of its ports is connected to conduit 11L as a pathway to valve 12$iii$, like the pathway between the first and second valve sets as in FIG. 2. While connected to conduit 11L, valve 12$i$ is also connected to conduit 11B, and conduits 11A and 11B can deliver or receive for pressurized fluid flow depending on whether the DCC Apparatus is operated in the forward flow or backflush mode. When valve 12$ii$ is in one state for connection to conduit 11S or column 16, it also is connected to either conduit 11E or through conduit 11T and valve 12$iii$ to conduit 11F, respectively. These connections through conduits 11E and 11F to columns 15 and 16 ar at the other end of both of the columns from the first above-described connections through conduits 11C and 11D, respectively. Actually in relation to FIG. 2, the three ports of valve 12$ii$ connected to conduits 11E or 11F, directly or indirectly, and to and from detector 17 along with valve 12$iii$ constitutes the second valve set 12B of FIG. 2. In addition, there may be present a detector isolation valve similar to that shown in FIG. 5 as valve 42 and connected in a similar fashion with detector 17 in conduits 11G and 11H. This configuration allows for the following conveyances: for a forward flow mode the following: system default, first column to detector, second column tod etector, first column to detector to second column, second column to detector to first column; for a backflush mode the following: first column, second column, and with the presence of a detector isolation valve backflushing of the second to first column.

FIG. 4 shows a possible addition to the dual column chromatographic apparatus which includes a precolumn in conduit 11J of FIG. 2. FIG. 4 shows 11J entering valve 29 where the valve is a four (4) port, bimodale valve known to those skilled in the art for use in pressurized fluid chromatography systems. Valve 29 can be connected for actuation to controller 13 by actuating connection 14I. From valve 29 conduit 11U is connected to precolumn 30 in the forward flow mode. This precolumn can be any guard column known to those skilled in the art to increase the life of the chromatographic analytical or preparative column by removign noneluting components and particulate material before it reaches the chromatographic analytical or preparative columns. The guard column has a stationary phase such as a microparticulate packing which can be any packing known to those skilled in the art for this purpose. The eluant from the guard column flows via conduit 11V to valve 29 for conveyance to conduit 11J. The conduits 11U and 11V when the precolumn is used in the apparatus constitute part of the fluid conduit assembly 11. The flow through the guard column is in the forward direction when the flowpath through the dual column is in the forward direction when the flowpath through the dual column chromatographic apparatus is in the forward flow mode. Also, the flowpaths through the precolumn from the valve 29 can be in the backflush mode through conduit 11V and out through conduit 11U when the DCC Apparatus is in the backflush flow path mode of operation. Such an arrangement even allows the guard column to be individually and separately backflushed when desired.

FIG. 5 presents a particular embodiment of the DCC Apparatus in a pressurized fluid chromatography system, where the fluid preferably is a liquid, although a gas could also be used. As in FIGS. 1–4 similar reference numbers in FIG. 5 refer to similar devices as in the other figures. One or more mobile phase reservoirs, 31 and 32 contain the same or different types or concentrations of liquid mobile phase solvents, 33 and 34 in FIG. 5. Although FIG. 5 depicts the use of two reservoirs, it is possible to use only one or more than two. When using a plurality of reservoirs, it is preferred to use two groups of reservoirs with three or more reservoirs in each group. The plurality of reservoirs is especially suitable in the case of gradient elution chromatography. The one or more mobile phases move through a conduit suitable for use in pressurized chromatography, conduits 35 and 36 in FIG. 5, to a solvent selection zone 37 for selection, mixing, or combining of the solvent mobile phases. Depending on flow requirements one or more pumps like pump 40 supplies the required pressure to the chromatographic system and moves the solvent mobile phase through the chromatographic system. For example, a separate pump can be used for each mobile phase, 31 and 32, respectively; or one pump can be used for a selected, mixed or combined solvent mobile fluid phase. The pump or pumps transport the mobile phase or phases individually and separately to the pressurized fluid chromatography apparatus of the phases can be combined by either flow programing or solvent programing otherwise usually referred to as gradient elution through the solvent selection zone 37. This zone can be connected for activation by electronic, pneumatic or hydraulic connection with controller 13 through connection 38. Preferably this controller is a computer with a program along with necessary flow control hardware to accomplish the desired solvent selection. Any computer and program and flow control hardware known to those skilled in the art can be used. In regards to the pumps, a nonexclusive example of a suitable pump is that known as a Bran and Luebbe Pump available from the Bran and Luebbe, Inc., Buffalo Grove, Ill. 60015. It is also possible to have closed loop (feed/back) flow controllers having a flow-through pressure transducer (not shown) to measure flow rate by measuring the pressure drop across a restricted area of a fixed valve. The flow rate can be signalled back to a control unit, like controller 13 which compares the actual flow rate with a pre-set flow rate and the motor speed or gas pressure on a pneumatic piston (not shown) is changed to offset any difference When the multiple solvents or mobile phases are mixed in a mixing chamber like 37 in FIG. 5, they are transported thereto by conduits 35 and 36, respectively. The mixed phases or a single mobile phase, in the case where the mixing of phases is not used, move through conduit 39 by the action of the one or more pumps for conveyance to the DCC Apparatus.

Additional features that the PFCS may have, although not shown in the drawing include modified solvent reservoirs, filters, and pressure indicators. The solvent reservoir may be adapted for solvent degasing by any method known to those skilled in the art. Filters may be located before and/or after the high pressure pump 40. Additionally, a pressure gauge may be located around the pump to indicate the pressure of the system, and a pulse dampener may be included after the pump to assuage the pulses produced by the pump. Sample injection pump 41 allows for injection of the sample into conduit 11A of the fluid conduit assembly for conveyance to the DCC Apparatus.

The preceding description of FIG. 5 presents one of many possible embodiments for a PFCS, the preferred PFCS is an, high pressure liquid chromatography system. The following continued description of FIG. 5 is for the preferred embodiment of the DCC Apparatus of the present invention.

The mobile phase and/or sample is conveyed through conduit 11A to an ingress-egress valve 20, which is connected to the controller 13 by actuating connection 14A.

The fluid conduit assembly or means is comprised of conduit piping connecting the dual columns, detector, multi-valve arrangement in a similar manner to that of FIG. 2 with three exceptions. First, the fluid conduit assembly in addition to conduits 11A through 11L as in FIG. 2, also has conduits 11X through 11Z and 11Z'. Second, there are two valves present in what conceptually can be referred to as each valve set 12A and 12B of FIG. 2. The third exception is the presence of an additional valve 42 that isolates the detector from the pressure of the DCC Apparatus Although valves 12$iv$ and 12$v$ can be indicated as being inthe valve set 12A of FIG. 2 and valves 12$vi$ and 12$vii$ can be indicated as being in the valve set 12B of FIG. 2, these valves may exist with independent identity from these valve sets. In other words these valves may be just aplurality of valves without valves 12$iv$ and 12$v$ as well as the two valves 12$vi$ and 12$vii$ perform the same function as valves sets 12A and 12B, respectively. Valve 42 is any multi-port and multimodal valve known to those skilled in the art as are valves 12$iv$ through 12$vii$, and valve 42 can be considered a part of the multi-valve arrangement 12. As with the DCC Apparatus of FIG. 2, that of FIG. 5 has each valve with an actuating connection with controller 13. So valve 20 is again connected to the controller 13 by actuating connection 14A as valves 12$iv$–12$vii$ and 42 are connected by connections 14J, 14K, 14L, 14M, and 14N, respectively. Valves 12$iv$ and 12$v$ are onnected together for pressurized fluid passage between them by conduit 11X, and in a similar manner valves 12$vi$ and 12$vii$ are connected by conduit 11Y.

Valves 12$iv$ through 12$vii$ and valve 42 are capable of routing liquid by two pathways in an unactuated state and two different pathways in an actuated state, where actuation is assisted by the controller 13 and transmitted by connectors 14A and 14J through 14N to the appropriate valves. In the following description in referring to onestate and the other state either state could be the actuated state while the other would be the unactuated state or vice versa. In a forward flow mode valve 12$v$ is connected to conduit 11J to receive the fluid mdbile phase with or without Sample. Valve 12$v$ in one state delivers these materials to column 15 and can conduct effluent from column 15, where the effluent is received from conduit 11K through valve 12$vi$ through conduit 11Y and valve 12$vii$, to valve 12$iv$. In another state this valve 12$v$ can deliver fluid mobile phase with or without sample from conduit 11J to valve 12$iv$ for conveyance to column 16, and it can convey the effluent from column 16 to column 15 through valve 12$vi$. Also in the forward flow mode valve 12$iv$ on one state receives the fluid mobile phase with or without Sample from valve 12$v$ via conduit 11X and conveys the same to column 16. While in this same state valve 12$iv$ channels fluid mobile phase with or without Sample or some separated constituents thereof from conduit 11L to conduit 11I for exit from the DCC Apparatus through valve 20 and conduit 11B to collection or waste. In its other state valve 12$iv$ redirects the contents of conduit 11L to conduit 11D for flow into column 16. While doing this, this valve provided by its other passageway an exit from the DCC Apparatus for the contents of conduit 11X, where 11X receives the contents of conduit 11K through valve 12$v$.

In the forward flow mode valve 12$vii$ receives effluent from column 15 by conduit 11E. From valve 12$vii$ in one of its states the contents of conduit 11E passes via conduit 11L to be collected after passing from the DCC Apparatus via conduit 11B by the valves being in the appropriate states. With valve 12$vii$ in its other state, the effluentfrom column 15 passes through conduit 11Y in pressurized fluid passage to valve 12$vi$. Also in this same state valve 12$vii$ by its other mode provides a passageway or channel from detector isolating valve 42. Valve 12$vi$ in one of its states receives the contents from conduit 11Y and directs it to conduit 11G. This conduit communicates in pressurized fluid fashion with anther port of valve 42. While in this state valve 12$vi$ provides a passageway from conduit 11F to conduit 11K. Valve 12$vi$ in its other state provides a passageway from conduit 11F for the effluent of column 16 to conduit 11G for conveyance to isolating valve 42. The other passageway of valve 12$vi$ in this state is from conduit 11Y to conduit 11K for conveyance to valve 12$v$.

As previously mentioned valve 42 is any multi-port, multi-modal valve known to those skilled in the art. This at least bi-modal valve provides pressurized fluid communication to deliver fluid mobila phase with or without sample with or without separated constituents thereof to detector 17 via conduit 11Z or 11Z'. The other conduit would provide an outlet passage from the detector 17 to valve 12$vii$. When valve 42 is in its other state, it provides a by-pass passageway between conduits 11G and 11H. Such a passageway is useful in backflushing.

In the backflush mode the pressurized fluid connections and passageways between the valves for both states of the valves and the fluid conduit assembly are the same, but the fluid mobile phase is provided to the DCC Apparatus by valve 20 to conduit 11I. Concomitantly the exit from the DCC Apparatus is through conduit 11J. In this manner of operation the delivery to and removal of effluent from the columns, 15 and 16, are at the opposite ends from that of delivery and removal of effluent in the forward flow mode. So delivery to column 15 is through conduit 11E and removal of effluent is by conduit 11C. Delivery to column 16 is by conduit 11F and removal of effluent is by conduit 11D.

With a multi-valve arrangement having four, 4-port, bimodal, and actuatable valves; an ingress-egress actuatable valve; and an detector isolating valve; a fluid conduit assembly; controller and actuating connections between the controller and each valve, where this all constitutes a fluid conveyance system, and with the 2 chromagraphic columns, a chromatographic detector, pump, mobile phase reservoir and sample injector, various configurations of operation in a forward and a backwashing application or mode are possible. The forward flow modes are: system bypass, column 15 to detector 17, column 16 to detector 17, column 15 to column 16 to detector 17, column 16 to column 15 to detector 17, column 15 to detector 17 to column 16, and column 16 to dete4tor 17 to column 15. The mode of operation in the backflush arrangement include: column 15, column 16 to column 15, column 15 to column 16, column 16. When a guard column or precolumn like that of FIG. 4 is connected to conduit 11J, as previously discussed, with the DCC Apparatus of FIG. 5, the precolumn can be individually loaded in forward flow or backflush mode with the proper arrangement of the multi-valve arrangement.

The by-pass operation for the DCC Apparatus of FIG. 5 has the mobile phase with or without sample injection passing through conduit 11A into valve 20 to conduit 11J to valve 12v. Valve 12v is in a state to conduct the fluid to conduit 11X to valve 12iv, which is in a state to conduct the fluid to conduit 11I to valve 20. This valve is actuated to conduct the fluid to conduit 11B for collection.

The mode of operation of the DCC Apparatus for column 15 to detector 17 in the forward flow mode (hereinafter referred to as Pathway B) initially involves pumping at least one mobile phase 33 or 34 with pump 40 with or without Sample via conduit 39 and 11A to valve 20. Valve 20 is in a state supplied by controller 13 through connection 14A to conduct the fluid through conduit 11J to valve 12v, and this valve is in a state supplied by controller 13 through connector 14K to conduct the fluid under pressure usually ranging from 500 to 2000 psi via conduit 11C to column 15. Column 15 has a stationary phase to result in different eluting constituents (separated) of the Sample. The eluant from column 15 flows under pressure and conduit 11E to valve 12vii which is in a state through controller 13 and connector 14M to conduct the fluid via conduit 11Y to valve 12vi. Valve 12vi is in a state through controller 13 and connectIon 14L to conduct the fluId to detector 17 via conduit 11G and valve 42 and conduIt 11Z. The detector 17 is preferably an ultraviolet detector and the flow from the detector is to valve 42 through conduit 11Z'. The flow from valve 42 is through conduit 11H to valve 12vii which is in a state through controller 13 by connector 14M for flow via conduit 11L to valve 12iv. Valve 12iv is in a state by controller 13 and connector 14J for delivery of the fluid to conduit 11I for conveyance to valve 20. Valve 20 is in a state by controller 13 and connector 14A to deliver the fluid to conduit 11B for conveyance to collection.

The operation of the system for column 16 to detector 17 (hereinafter referred to as Pathway C) involves the same flow path as aforedescribed for Pathway B up until valve 12v In this instance valve 12v is in a state through 13 and 14K to deliver the fluid to conduit 11X which conducts the fluid to valve 12iv. This valve is in a state to convey the fluid to conduit 11D for delivery to column 16. Column 16 can be similar to column 15 and preferably is and column 16 has a stationary phase or packing which is similar to or different from that of column 15 although, preferably, it is the same. The eluant from column 16 passes through conduit 11F to valve 12vi which is in a state through 13 and 14L for delivery of the fluid through conduit 11G to valve 42. This valve is in a state through 13 and 14N to convey through conduit 11z to detector 17. The fluid passes from detector 17 via conduit 11Z' to valve 42 and conduit 11H to valve 12vii which is in a state through 13 and 14M for delivery of the fluid to conduit 11L. The fluid ends up at valve 20 which is actuated in a state for delivery of the fluid to collection as aforedescribed for Pathway B.

In the forward flow operational mode from column 15 to column 16 to detector 17 (hereinafter referred to as Pathway D), the pathway is identical to that of the aforedescribed Pathway B up until valve 12vi. Instead of this valve delivering the fluid from conduit 11Y to the detector, the valve is in a state by controller 13 and connector 14L to deliver the fluid via conduit 11K to valve 12v. Valve 12v is in a state by controller 13 and connector 14K to deliver fluid to conduit 11X for conveyance to column 16 through valve 12iv and conduit 11D as aforedescribed in Pathways B or G. The flowpath from column 16 in this Pathway D is that identical to aforedescribed Pathway C for transmission of the fluid through detector 17 and to collection.

The forward flow mode of operation for conveyance to column 16 to column 15 to detector 17 (hereinafter referred to as Pathway E) involves pumping the fluid from pump 40 through conduit 11A with or without a sample injection from sample injector 41 to column 16 as in Pathway C. The eluant from column 16 carried in conduit 11F to valve 12vi. This valve is in a state by controller 13 and connector 14L so that the fluid eluant is delivered through conduit 11K to valve 12v. Valve 12v is in a state to deliver the fluid via conduit 11C to column 15. The pathway through column 15 to the detector 17 to collection is identical to that of the aforementioned pathway B.

The flow pathway through column 15 to dector 17 to column 16 (hereinafter referred to as Pathway F) is identical to the aforementioned Pathway B for passage of the fluid to column 15 to detector 17. A difference occurs where the fluid is conveyed to column 16 through valve 12iv in a state to deliver the fluid via conduit 11D. The pathway of the fluid eluant from column 16 is via conduit 11F to valve 12vi which is in a state by controller 13 and connector 14L for delivery of the fluid via conduit 11K to valve 12v. Valve 12v is in a state by controller 13 and connector 14K to deliver the fluid to conduit 11X to valve 12iv. This valve is in a state by 13 and 14J to deliver the fluid to conduit 11I and through valve 20 to conduit 11B for collection.

The flowpath to column 16 to detector 17 to column 15 (hereinafter referred to as Pathway G) at the beginning is identical to Pathway C for passage to column 16 to detector 17. The effluent from detector 17 travels by conduit 11Z' to valve 42 and conduit 11H to valve 12vii, and this valve is in a state by 13 and 14M for passage of the fluid via conduit 11Y to valve 12vi. Valve 12vi is in a state by 13 and 14L to deliver the fluid via conduit 11K to valve 12v. Valve 12v is in a state by 13 and 14K to deliver hte fluid via conduit 11C to column 15. The eluant from column 15 passes through conduit 11E to valve 12vii, and this valve is in a state by 13 and 14M to convey to conduit 11L for conveyance to valve 12iv. Valve 12iv is in a state by 13 and 14J to convey the fluid via conduit 11I to valve 20 for passage to collection in an identical manner to that of Pathway B through E.

The backflush pathways include the backflush of column 15, where the mobile phase of 33 and/or 34 Without a sample in conduit 11A is pumped by pump 40 to valve 20, and this valve is in a state by controller 13 and connector 14A for passage of the mobile phase through conduit 11I to valve 12iv. This valve is in a state by 13 and 14J to pass the mobile phase to valve 12v through conduit 11X which is in a state by 13 and 14K to pass the mobile phase via conduit 11K to valve 12vi. Valve 12vi is in a state by 13 and 14L to convey the mobile phase through conduit 11Y to valve 12vii, and this valve is in a state by 13 and 14M to transmit the mobile phase via conduit 11E to column 15. Mobile phase travels through the stationary phase of column 15 and out through conduit 11C to valve 12v. Valve 12v is in a state by 13 and 14K to conduct the mobile phase to conduit 11J to valve 20. Valve 20 is in a state by 13 and 14A to convey the mobile phase to collection via conduit 11B. This pathway is hereinafter referred to as 'Pathway BA".

Another backflush pathway is from column 16 to column 15. This pathway is identical to Pathway BA up until valve 12vi. At this valve, which is in a state by 13 and 14L, the mobile phase flows through conduit 11F to column 16. Mobile phase passes through column 16 and out conduit 11D to valve 12iv. The valve 12iv is in a state by 13 and 14J so that the mobile phase flows through conduit 11L to valve 12vii. Valve 12vii is in a state by 13 and 14M to transmit the mobile phase via conduit 11E to column 15. Mobile phase flows through the stationary phase of coduit 15 and out conduit 11C and to collection in an identical manner to the aforeuescribed Pathway BA. This pathway is hereinafter referred to as 'Pathway BB'.

The pathway for backflushing column 15 to column 16 (hereinafter referred to as 'Pathway BC') involves pumping the mobile phase via conduit 11A without a sample to valve 20 which is in a state to convey the mobile phase via conduit 11I to valve 12iv. Valve 12iv is in a state for passage of the mobile phase via conduit 11L to valve 12vii. Valve 12vii is in a state to pass the mobile phase to conduit 11E so that the mobile phase passes into column 15 and through the stationary phase and out conduit 11C to valve 12v. Valve 12v is in a state to pass the mobile phase to valve 12vi. Valve 12vi is in a state to conduct the fluid to conduit 11F and through column 16 and out conduit 11D to valve 12iv. Valve 12iv is in a state to conduct the mobile phase through conduit 11X to valve 12v for conveyance through conduit 11J to valve 20. Valve 20 is in a state to conduct the fluid to collection via conduit 11B.

The flow pathway for backflushing column 16 (hereinafter referred to as 'Pathway BD') involves pumping of the mobile phase to valve 12vii in a similar fashion to that of aforedescribed Pathway BC. Valve 12vii is in a state to deliver the mobile phase to valve 42 via conduit 11H. The mobile deliver to conduit 11G and to valve 12vi which is in a state to delivery the mobile phase to column 16 via conduit 11F. The mobile phase flows through column 16 and exits via conduit 11D. The mobile phase travels to valve 12iv which is in a state by 13 and 14J to convey the mobile phase via conduit 11X to valve 12v. Valve 12v is in a state by 13 and 14K to deliver the mobile phase to conduit 11J for conveyance to collection in an identical manner to that of the aforedescribed Pathway BC.

The backwash flow path for column 15 to column 16 (hereinafter referred to as Pathway BE) involves pumping the mobile phase to valve 12vi in a manner identical to that for Pathway BD. Here valve 12vi is in a state so that the mobile phase flows through conduit 11Y back to valve 12vii which is in a state for the mobile phase to flow in conduit 11E to column 15. The mobile phase flows through column 15 and exits via conduit 11C in which the mobile phase flows to valve 12v. Valve 12v is in a state so that the mobile phase flows in conduit 11K to valve 12vi which has the bimodal path to conduit 11F so the mobile phase flows into column 16. The mobile phase flows to the stationary phase in column 16 and exits via conduit 11D to valve 12iv which has the bimodal pathway to conduit 11X to valve 12v. Valve 12v has the bimodal pathway to valve 11J for deliver of the mobile phase to collection in a similar manner to that for Pathway BD.

The aforedescribed pathways show that the valves are in their particular states through controller 13 and the appropriate actuating connector so as not to disrupt the continuous pressurized flow. If the valves are to be actuated to another state for the particular pathway, this is done at a time other than during the operation of a pathway. The bimodal valves are set for a particular pathway and not actuated until a different pathway is desired.

The preferred process of using a with the DCC Apparatus of the present invention is for separating two overlapping peaks of interest in a Sample. This is accomplished in accordance with FIG. 5 utilizing the guard column 30 design that is depicted in FIG. 4 connected with conduit 11J which is the preferred embodiment of the present invention The column configuration is switched from the system bypass pathway to a pathway to equilibrate the precolumn 30 and columns 15 and 16 of FIGS. 4 and 5 so that the supports in the columns can be equlibrated (with or without detector). A sample is injected by injector 41 into conduit 11A and pumped along with the at least one mobile phase to the precolumn 30 through valve 20 and conduit 11J and valve 29 and conduits 11U and 11V. The sample is eluted through the precolumn and onto chromatographic column 15 by forward Pathway B while the precolumn 30 is switched out of the chrbmatographic flow pattern by actuating valve 29 by controller 13 through connector 14A to another state of passageway. A quickly eluting impurity peak is resolved and collected with the "to be recovered" eluant. As the two peaks of interest are to elute from the column 15, a small fraction of the first peakis collected through conduit 11B. The valves are placed in a state by controller 13 and the appropriate actuating connections of 14 to change the column configuration from Pathway B to Pathway F. When the two peaks of interest have been completely eluted onto column 16, the controller 13 through appropriate actuating connections provides states of passageways for the valves to switch the column configuration to backflush Pathway BA to remove slowly eluting contaminants. Afterwards, column 15 is equilibrated with mobile phase.

The controller 13 through appropriate actuating connectors provides the states for the valves to give a column configuration of Pathway C to elute the materials of interest from column 16. As the peaks begin to elute from column 16, another small fraction of the first component is collected through conduit 11B. Again, the state of the valves is set by controller 13 through appropriate connectors of 14 to provide a column configuration to Pathway G. As the last of the material elutes from column 16, a trailing fraction of the second component is collected. Once again, the state of the valves is set by controller 13 through appropriate connectors 14 to produce a column configuration having Pathway BD for backflushing. After backflushing the state of the valves is set to forward Pathway C to reequilibrate column 16.

The chromatographic resolution is finally completed by eluting materials of interest through both of the columns by having the states of the valves set through controller 13 and appropriate ctuating connections 14 to produce a column configuration of Pathway D or F. Product bearing fractions are collected through conduit 11B. The states of the valves are set by the controller and appropriate actuating connectors 14 to produce a column configuration of backflush BB while also backflushing the precolumn 30 through conduit 11J and 11V and 11U to provide for backflushing of all the columns in one pathway. The states of the valvesare set by the controller 13 by appropriate actuating connectors 14 to effect a column configuration which is the system bypass or now referred to as Pathway A.

In the preferred embodiment of the present invention as depicted in FIG. 5 with the precolumn of FIG. 3 connectad to conduit 11J, the columns are those of U.S. Pat. No. 4,582,608 including the precolumn and the stationary phases are of the silica type. The detector is an ultraviolet detector. The pressure of the system is in the range of up to 2000 psi, and the has a dual pump configuration, and the system is operated in a forward approach as to a reverse phase approach with one type of mobile phase. The aforementioned type of pump is useful even though any of the constant volume, constant displacement, or constant pressure pumps known to those skilled in the art can be used along with any pulse dampening devices known to those skilled in the art. The controller in the preferred embodiment for the DCC Apparatus is a part of the controller for the , where the meaning of the terminology "by part" in this instance means that one or more computer programs in a personal computer for the control the DCC Apparatus. The one or more program would have the below-described structure, sequence and it or feel.

DCC Apparatus Control

Copyright Separation Technology Inc. 1989

The program for the column switching code can be written into three separate functioning portions. The first allows for set up of the desired controls needed for the column switching package. The second allows the operator to indicate how and when the column switching will occur. The third correctly controls the switching valves after error checks are parformed.

The set up portion of the code is written as a separate program. This program forms a data file that controls the configuration of column switching operations. The set up program allows Lonfiguration of up to 36 column control numbers. Each column control number can operate up to 36 valves and/or switches. Three types of operationn are available: (1) close the valves and/or switch, (2) open the valves and/or switch or (3) maintain the present settings. The set up pseudo code is as follows:

1. Read the set up data file into memory;
2. Display the data on screen;
3. Allow cursor movement to any portion of the 36 column control number/36 switch settings matrix;
4. Allow the operator to change/enter a numeric 1 or 0 to signal a close or open operation respectively. Also, a blank can be entered to signal no change from a previous condition when called;
5. The operator can enter a control type for each switch: "M" momentary contact operates for a specific time interval; "L" latching contact operates until asked to change by another column switching operation; "T" toggling contact operates only while signaled by the TurboPrep ® controls;
6. The operator can enter a delay time for each switch operation;
7. The operator can enter the momentarv contact time if used; and
8. Allow saving of the data to a set up data file on disk.

The control initiation portion of the code allows the operator to request column switching by one of numerous methods. The column switching can be prompted by time, data input slope value, and/or external contact closure. Each of these requests is entered on an interactive screen. These requests can be written into an operation program or made directly during real time operations.

When a request is made, this portion of the software monitors for the correct time, slope or external input. If the correct control is sensed, the corresponding column switching event is signaled. The pseudo code for this operation is as follows;

1. At the start of a program read in the control program if one is indicated.
2. If a programmed column switching event starting time has come, go to 8.
3. Monitor for operator key strokes during real time control.
4. If an entry is made in the control event fields, check for
5. If there are errors, signal the operator with an error message
6. If the entry is in the correct range, input the data into control memory.
7. If the data entry is an immediate operation request, signal for the desired column switching.
8. If the starting time for the column switching event has come, look at the type of operation requested.
   (a) If a real time operation, signal for the desired control.
   (b) If an ascending slope operation,
      (1) calculate the ascending slope value
      (2) if the ascending slope value is equal to or higher than requested slope singal and the previous calculated slope value was less than the requested slope signal, signal for the desired control.
   (c) If a descending slope operation, (1) calculate the descending slope value
(2) if the descending slope value is equal to or higher or more negative than the requested slope signal and the previous calculated slope value was less than the requested slope signal, indicate that the descending slope has occurred
(3) if the desired slope has occurred and the ending slope is less than the requested ending slope, signal for the desired control.

(d) If an external contact closure operation,
(1) determine if the externalcontact is closed
(2) if the external contact closure is closed, signal for the desired control.

(e) If a time from the last ascending slope operation,
(1) determine the elapsed time since the last ascending slope
(2) if the elapsed time is equal to or more than the desired elapsed time, signal for the desired control.

(f) If a time from the last descending slope operation,
(1) determine the elapsed time since the last descending slope
(2) if the elapsed time is equal to or more than the desired elapsed time, signal for the desired control 9. If the operation is signalled for and was called by a real time interactive request, enter values as follows:
(a) If an ascending or descending slope request and the slope value is not entered by the operator, then fill in the slope value with the calculated slope.
(b) If a timed operation, fill in the slope value with the calculation slope.
(c) If a time from the last ascending or descending slope operation and the start time is not entered, calculate the elapsed time from the last ascending or descending slope respectively and enter it into the start time.
(d) if a real timed operation and the start time was not entered by the operator, enter present time into the start time
(e) if the end time value was not entered by the operator
(1) add the set window time to the start time
(2) enter this calculated value as the end time.

10. If the event has operated, flag this operation to prevent reoperation.

11. If the event has operated, and the next sequential event has a blank start time, transfer control to that event and go to 8.

The column switching control portion o the code operates the correct switches/valves if no errors are detected. Because column switching must override any previous column lineups, conflicts are signaled and messages to this effect are given to the operator.

When the control initialization signals for a column switching event, the control portion determines the subgroup it belongs to. If the subgroup conflicts with presently operating controls, the operator is informed with an error message. If numerous columns configurations are requested at the same time, the first called is used and the others ignored In the manual control portion of the program the operator is allowed to override the previously operating column.

When an oparation is implemented, the set up data is used to determine which switches to control. A control event symbol "1" will close a switch/valve, a "0" will open a switch/valve and a blank will maintain the present position.

The following pseudo code is used when signaled by the initialization portion of the code.

1. At the start of the TurboPrep TM program the set up data file is read into memory.
2. If signaled, operation is a member of a subgroup (column switching events are all subgroups #1);
   a. Determine if another control of the same subgroup is presently operating.
   b. If another member of the same subgroup is operating and the program is in manual mode, give a TurboPrep TM message "more than one column event requested do you wish to continue (Y/N)".
      (1) If the operator answers (Y)es, the manual screen highlight is moved to the requested column control number.
      (2) If the operator answers with anything but (Y)es, the operation is ignored.
   c. If another member of the same subgroup is in operation and the TurboPrep TM ) program is in method development (interactive process control with run program abilities),
      (1) if the request was made n real time interactively by the operator, ignore the operation, display a message and beep. The message reads "Cannot operate two column events at the same time."
      (2) If the request was a programmed call, ignore the operation, display a message and beep. The message reads "Conflicting control events called, event # ignored" where # is the number of the control event that was requested. The previous event in the same subgroup maintains its positioning.
3. If the signaled operation is not a member of a subgroup or there is not a subgroup conflict:
   a. Send the corresponding signals to the switches/valves as indicated in the set up data for the called control event number.
   b. Highlight the operating control event on the screen.
   c. Mark the operation on the plot screen with a pip mark at the time of operation.
      (1) If a slope operation, place the pip on the corresponding detector's plot (can have up to three detector inputs)
      (2) If not a slope operation, place the pip on the number one detector's plot.
4. If the operation has taken place, flag its operation.

In the aforedescribed structure and approach of a computer program, the reference to a Turboprep TM program is to a copyrighted computer program available from Separations Technology Inc., 2 Columbia Street, Wakefield, R.I. 02879. The program for control of the DCC Apparatus can be written in any convenlent level computer language, although the Pascal language is preferred, and the computer can be any personal computer, although the AT models from IBM or compatibles are preferred. Also it is preferred that other programs run on the PC computer to provide control for other steps in the HPLC.

We claim:
1. A dual chromatographic column apparratus with multiple valves for column switching useful with pressurized fluid cnromatography devices, comprising:
   (a) a first and second chromatographic column having two ends, where each column is adapted for: (i) holding a charge of a solid stationary phase, (ii) operating under superatmospheric pressures, (iii) receiving mobile phase with or without a multi- constituent sample at one end, (iv) exiting at the other end mobile phase without or with sample which has at least one cnstituent eluting differently from the rest of the sample, and (v) backflushing with mobile phase;

(b) a detector adapted to receive mobile phase with or without sample from either or both of the columns sequentially or from a mobile phase reservoir through pressurized fluid communication with the columns or reservoir, (c) a fluid conveyance system having:
  (1) multi-valve arrangement, where each valve is adapted for actuation so the arrangement can be adapted for pressurized fluid communication with the columus and the detector to provide
    (i) for passage of the mobile phase with or without sample into the dual chromatographic column apparatus rather than by-passing this apparatus and for a forward flow mode with the capability for: selection of at least one column for flow with the detector, re-direction to the other column in at least one direction after passage through the detector, and recycling for up to both columnus and, (ii) for passage of mobile phase in a backflushing mode with the capability for backflushing at least both columns sequentially and each separately;
  (2) fluid conduit assembly to provide pressurized fluid communication between the valves of the multi-valve arrangement, the two chromatographic columns and the detector sequentially in series as follows: into the multivalve arrangement ,from and to the multi-valve arrangement and the first column, from and to the multi-valve arrangement and the detector, from and to the multi-valve arrangement and the second column, and out of the multi-valve arrangement and between the valves in the multi-valve arrangement to accomplish such communication;
  (3) controller in communicative relation with the actuators of each valve in the multivalve arrangement to at least transmit a signal to one or more of the valves at various times to establish at least the (i) pressurized fluid communication for mobile phase witn or without sample into the multi-valve arrangement, (ii) sequence of column selection and redirection in the forward flow and backflush modes to provide for the configuration changes to the dual column apparatus, and (iii) pressurized fluid communication for at least mobile phase with or without sample or constituents of the sample for collection or for waste.

2. The apparatus of claim 1, wherein the detector has two connections through the fluid conduit assembly to the second set of valves in the multi-valve arrangement where one connection allows for ingress and the other for egress from the detector and the fluid flow through the detector is in one direction.

3. The apparatus of Glaim 1, wherein the fluid is a liquid so that the apparatus provides the chromatographic columns for a pressure liquid chromatography device having at least one pump for pressurized flow of fluid and sample sample injection meana for a multi-constituent sample at least one fluid phase carrier reservoir, controller for controlling the pressure and fluid flow into the apparatus, and a collection means for collecting fluid phase carrier with or without the multi-constituent sample or separated constituents of the sample.

4. The apparatus of claim 1, wherein the controller is at least a part of a programmable controller for a pressurized fluid chromatographic system, where the controller controls functions in addition to the valve switching of the dual column apparatus.

5. The apparatus of claim 1, which includes a guard chromatographic column having a charge of stationary phase to separate any column contaminants from the multi-component sample, and operating under superatmospheric pressures, and connected for pressurized fluid communication with the fluid conveyance system through the multi-valve arrangement prior to the first and second chromatographic columns.

6. The apparatus of claim 5, which includes a multi-position multi-modal valve connecting the guard column with the fluid conveyance system through the fluid conduit assembly through which one port of the valve is connected to receive under pressure fluid mobile ohase with or without multicomponent sample and through which another port is connected to deliver the same material received by the valve to the guard column and through which another port is connected to receive the mobile phase without sample or with multi-component sample having some components eluting from the column at different intervals, and through which another port of the valve delivers the same material received from the guard column to a port in one of the valves of the first multi-valve arrangement.

7. The apparatus of claim 6, which includes an ingress and egress valve connected to the fluid conduit assembly to by-pass the apparatus in one state of the valve and to convey under superatmospheric pressure fluid phase with or without multi-component sample to a port in the multi-position, multi-modal valve connecting the guard column to the fluid conveyance system for delivery to the guard column.

8. Apparatus of claim 1, wherein the multi-valve arrangement is comprised of:
  (a) a first set of more than one valve adapted for pressurized fluid communication in a forward mode to provide for the capability of pressurized fluid communication of the mobile phase with or without sample to substantially all of the following: (i) for receipt of mobile phase with or without sample through a valve into the dual column apparatus rather than by-passing the apparatus, (ii) by selection to one of the columns, (iii) by redirection to one end of at least one other column upon receipt from the first column from a second arrangement of more than one valve, and (iv) by exiting from the apparatus the delivery of the mobile phase with or without at least portions of sample to collection or waste; adapted for allowing for backflushing of at least one column; and adapted for pressurized fluid communication in a forward and backflushing mode for mobile phase with or without sample with a second arrangement of more than one valve;
  (b) a second set of more than one valve adapted for pressurized fluid communication of mobile phase witn of without a sample to the first valve set in both a forward and backflushing mode and for redirection to one column from the other column or the detector, and wherein the fluid conduit assembly provides pressurized communication between the valves in conjunction with the controller that communicates with the actuators of the valves in both the first and second valve sets.

9. Apparatus of claim 8, wherein the first set of valves and the fluid conduit assembly are connected to provide fluid pressurized communication for mobile phase with or without sample to one or both columns sequentially, where this latter communication is accomplished from at least one connection between the first and the second valve sets and the second valve set is connected with the other end of the column that is connected with the first valve set to re-direct the fluid frm the one column to the other column.

10. Apparatus of claim 9, wherein the first and second valve sets each have two 4-way, bimodal vales; and wherein the fluid conduit assembly provides for pressurized fluid communication of mobile phase with or without multi-component sample for receipt by the apparatus and with these valve arrangements
   (a) through the first valve set by connection with one of the ports of one of the four-port valves and for communication for transport the same valve in the first valve set has ports connected through the fluid conduit assembly as follows: to one of the dual columns, to the other valve in the first valve set, to one of the valves in the second valve set; and the other valve in the first valve set has ports connected through the fluid conduit assembly as follow: from the other valve in the first valve set, to apparatus outlet in a forward flow mode an dinlet for backflushing mode, to another valve in the second valve set, and to one end of the other column; and
   (b) through the second valve set by connection for communication by transport where one valve has a port connected to the valve in the first valve set that receives for the apparatus, and another port connected to the other valve in the second valve set, and another valve connected to the other end of a column from that end to which the valves in he first valve set are connected, and the other port is connected to the detector and the other valve in the second valve set in addition to its connection to the first valve in that set has connections at different ports to: the other column at the end different from that to which the valves of the first set are connected, and the other end of the detector from that which the first valve of this set is connected and to the other valve in the first valve set from which the first valve of this set is connected.

11. Apparatus of claim 9, wherein each four port valve is two three-way valves.

12. Apparatus of claim 8, wherein the first valve set has one four-way bimodal valve and three adjacent ports of a six-way bimodal valve, and wherein the second valve set has a four-port bimodal valve and the other three adjacent ports of the six-port modal valve, and wherein the fluid conduit assembly provides for pressurized fluid communication:
   (a) in the first set for mobile phase with or without sample for receipt by the apparatus to one port of the six-port valve and from another port of the six-port valve in one of the valve's states to a port of the four-port valve and in another state of the six-port valve to one of the columns and in the first state of the four-port from a port in the four-port valve to the other column and in the other state of the four-port to exit for apparatus by-pass and where the second channel of the four-pot in one of the valve'sstates communicates with the second valve set and the exit from the apparatus; and
   (b) in the second set provides for mobile phase without sample or with a degree of separated sample from the column communicating with the six-port valve in the first set in hat valves first state to a port of the four-port of the second assembly in that valve's first state to another port in the six-port valve where this port is in the second assembly and to the detector and from the detector to the second channel of the four-port valve of the second set and to communication with the second channel of the four-port valve of the first set for exit from the apparatus and where the first set communicates with the other column another port of the six-port valve in the second set communicates with this second column and with the detector in the six-port valve's second state and from the detector to the four-port valve of the second set where the valve in its second state has delivered the sample with a degree of separated components to communication with the first set and exiting of the apparatus and where that four-port valve in its first state communicates with the first column and the output of that column communicates through the four-port valve of the second set with the first set for exit from the apparatus.

13. Apparatus of claim 12, wherein each four port valve is two three-way valves.

14. Apparatus of claim 8, which includes in addition to the two valve arrangements an ingress and egress valve connected be the fluid conduit assembly to by-pass the apparatus in one state of the valve and to convey fluid phase with or without multi-component sample to a port in one of the valves in the first valve set and from a port in another valve in the same valve arrangement.

15. The apparatus of claim 8, which includes a multi-position, multi-modal valve in the second set of valves in the.multi-valve arrangement to isolate the detector from the superatmospheric pressure of the apparatus.

16. The apparatus of claim 8, wherein each column has one connection through the fluid conduit assembly to each set of the multi-valve arrangement.

17. The apparatus of claim 8, wherein the fluid conduit assembly connects the detector to the second set of valves in the multi-valve arrangement through a bleed stream to protect the detector from the superatmospheric pressure of the apparatus.

18. A dual chromatographic column apparatus with multiple valves for column switching useful with pressurized fluid chromatography devices having at least one pump for pressurized flow of fluid and multi-constituent sample, sample injection means for the multi-constituent sample, at least one fluid phase carrier reservoir, and a controller for controlling the pressure and fluid flow in the chromatography device, comprising:
   (a) a first and second chromatographic column having two ends, where each column is adapted for: (i) holding a charge of a solid stationary phase, (ii) operating under superatmospheric pressures, (iii) receiving mobile phase with or witnout a multi-constituent sample at one end, (iv) exiting at the other end mobile phase without or with sample having at least one constituent eluting differently form the rest of the sample, and (v) backflushing with mobile phase;

(b) a detector adapted to receive mobile phase with or without sample from either or both, in series, of the columns or from a mobile phase reservoir through pressurized fluid communication with the columns or reservoir, (c) a fluid conveyance system having:
   (1) multi-valve arrangement, where each valve is adapted for actuation so the arrangement can be adapted for pressurized fluid communication with the columns and the detector, wherein the multi-valve arrangement is comprised of:
      (a) a first set of more than one valve adapted for pressurized fluid communication in a forward mode for receipt of mobile phase with or without sample from the ingress egress valve and for the capability of pressurized fluid communication of the mobile phase with or without sample to substantially all of the following: (i) by selection to one of the columns, (ii) by redirection to one end of at least one other column upon receipt from the first column from a second set of more than one valve, and (iii) by exiting from the apparatus the delivery of the mobile phase with or without at least portions of sample to collection or waste; adapted for allowing for backflushing of at least one column; and adapted for pressurized fluid communication in a forward ann backflushing mode for mobile phase with or without sample with a second set of more than one valve;
      (b) a second set of more than one valve adapted for pressurized fluid communication of mobile phase with of without a sample to the first valve set in both a forward and backflushing mode and for redirection to one column from the other column or the detector, wherein the detector is connected through the fluid conduit assembly by two connections for ingress and egress of fluid flow from the second valve set but isolated from the pressure of the apparatus; and wherein the detector has two connections through the fluid conduit assembly to the second multi-valve arrangement where one connection allows for ingress and the other for egress from the detector and the fluid flow through the detector is in one direction, wherein the fluid conduit assembly provides pressurized communication between the valves in conjunction with the controller that communicates with the actuators of the valves in both the first and second valve sets; so that, the multi-valve arrangement provides: for passage of the mobile phase with or without sample into the dual chromatographic column apparatus rather than by-passing this apparatus and for a forward flow mode with the capability for; selection of at least one column for flow with the detector, re-direction to the other column in at least one direction after passage through the detector including redirection to one or both columns sequentially, where this latter communication is accomplished from at least one connection between the first and the second valve sets and the second valve set is connected with the other end of the column that is cornnected with the first valve set to re-direct the fluid from the one column to the other column, and recycling for up to both columns and, ii)for passage of mobile phase in a backflushing mode with the capability for backflushing at least both columns sequentially, and, wherein each column has one connection through the fluid conduit assembly to each of the multi-valve arrangements;
      (c) an ingress and egress valve connected to the fluid conduit assembly to by-pass the apparatus in one state of the valve and to convey fluid phase with or without multi-component sample to a port in one of the valves in the first valve set and from a port in another valve in the same valve arrangement.
   (2) fluid conduit assembly t provide pressurized fluid communication between the valves of the multi-valve arrangement, the two chromatographic columns and the detector sequentially in series as follows: into the multivalve arrangement, from and to the multi-valve arrangement and the first column, from and to the multi-valve arrangement and the detector, from and to the multi-valve arrangement and the second column, and out of the multi-valve arrangement and between the valves in the multi-valve arrangement to accomplish such communication;
   (3) programmable controller means that can be at least a part of the controller for the chromatographic device and that is in communicative relation with the actuators of each valve in the multivalve arrangement to be capable of at least transmitting a signal to the actuators of each valve in the multivalve arrangement to establish through actuating one or more valves at various times at least the (i) pressurized fluid communication for mobile phase witn or without sample into the multi-valve arrangement, (ii) sequence of column selection and redirection in the forward flow and backflush modes to provide for the configuration changes to the dual column apparatus, and (iii) pressurized fluid communication for at least mobile phase with or without sample or constituents of the sample for collection or for waste.

19. The apparatus of claim 18, which includes a guard chromatographic column having a charge of stationary phase to separate any column contaminants from the multi-component sample, and operating under superatmospheric pressures, and connected for pressurized fluid communication with the fluid conveyance system through the multi-valve arrangement prior to the first and second chromatographic columns.

20. The apparatus of claim 19, which includes a multi-position multi-modal valve connecting the guard column with the fluid conveyance system through the fluid conduit assembly through which one port of the valve is connected to receive under pressure fluid mobile phase with or without multicomponent sample and through which another port is connected to deliver the same material received by the valve to the guard column and through which another port is connected to receive the mobile phase without sample or with multi-component sample having some components eluting from the column at different intervals, and through which another port of the valve delivers the same material received from the guard column to a port in one of the valves of the first multi-valve arrangement.

21. The apparatus of claim 20, which includes an ingress and egress valve connected to the fluid conduit assembly to by-pass the apparatus in one state of the valve and to convey under superatmospheric pressure fluid phase with or without multi-component sample to a port in the multi-position, multi-modal valve connecting the guard column to the fluid conveyance system for delivery to the guard column.

22. The apparatus of claim 18, wherein each column has one connection through the fluid conduit assemhly to each of the multi-valve arrangements.

23. The apparatus of claim 18, wherein the fluid conduit assembly connects the detector to the second multi-valve arrangement through a bleed stream to protect the detector from the superatmospheric pressure of the apparatus.

24. The apparatus of claim 18, wherein the detector has two connections through the fluid conduit assembly to the second multi-valve arrangement where one connection allows for ingress and the other for egress from the detector and the fluid flow through the detector is in one direction.

25. The apparatus of claim 18, wherein the fluid is a liquid so that the apparatus provides the chromatographic columns for a pressure liquid chromatography device having at least one pump for pressurized flow of fluid and sample, sample injection means for a multi-constituent sample, at least one fluid phase carrier reservoir, controller for controlling the pressure and fluid flow into the apparatus, and a collection means for collecting fluid phase carrier with or without the multi-constituent sample or separated constituents of the sample.

26. A dual chromatographic column apparatus with a plurality of valves having column switching capability for a pressurized fluid chromatography system comprising:

(a) a first and second tubular column each adapted for holding a charge of solid stationary phase and for operation at superatmospheric pressures, (b) at least one detector adapted for analysis of multi-constituent sample that has constituents separated by elution through at least one column, (c) a multi-modal valve with an actuator to deliver through one mode fluid mobile phase with or without multi-constituent sample to the apparatus and to receive from the apparatus fluid mobile phase with or without sample having some separated constituents, where the mobile phase is delivered to the apparatus in a forward flow or backflush mode;

(d) at least 4 valves that are at least bimodal with each having at least four ports and an actuator to change the valve state from one mode to another to accomplish at least the switching of the passage of fluid under pressure from a by-pass mode to an inlet mode into the apparatus to the first column to detector, the second column to detector, the first to second column to detector, the second column to first column to detector, the first column to detector to the second column, and for backflushing the first column, the second column to the first column, the first column to the second column, the detector to the second column, the detector to the first column to the second column, and the detector to the second column to the first column, (e) a fluid conduit assembly to provide for passage of a fluid under pressure from an ingress-egress valve to one or both columns and the detector in the aforementioned modes of operation, where the valves can be switched by actuators to change the configuration of the fluid flow path between the columns and the detector, wherein each of the four valves are connected to the dual column and the detector and the ingress-egress valve through the fluid conduit assembly as follows;

(1) a first four-port, bimodal valve has ports connected to: the ingress-egress valve and switched between: one of the dual columns, a second valve, with another valve other than the second valve switched to the converse;

(2) a second valve has ports connected to: the ingress-egress valve at a port other than that to which the first valve is connected switched between: the first valve, and another of the four four-port, bimodal valves different from that to which the first valve is connected, with the other column switched to the converse;

(3) a third valve has ports connected to and switched between: the first valve at the same port by which the first valve is connected to the valve other than the second valve, a column at an end other than that to which the first or second valve is connected, a port on the detector, and to a port on the fourth valve;

(4) a fourth valve has ports connected to and switched between: the third valve at the same port by which the third valve is connected to the fourth valve, the other column at the other end to which the first or seond valve is connected, another port on the detector, and the second valve at the port by which the second valve is connected to the valve that is other than the first valve, and wherein the third valve is connected to the other end of the column that is connected at the other end of that same column to the valve to which the third valve lacks a connection, and wherein the fourth valve is connected to the other end of the other column, which has a connection at the other end of that same column to the valve other than the ingress-egress valve to which the fourth valve lacks a connection; and (f) controller for generating process signals and for transmitting, and receiving signals to and from the actuators of each valve in the multivalve arrangement to establish at least the (i) pressurized fluid communication for mooile phase with or without multi-component sample into the multi-valve arrangement, (ii) sequence of column selection and redirection in the forward flow and backflush modes to provide for the configuration changes to the dual column apparatus, and (iii) pressurized fluid communication for at least mobile phase with or without sample or constituents of the sample for collection or for waste; and (g) a guard chromatographic column having a charge of stationary phase to separate any column contaminants from the multi-component sample, and operating under superatmospneric pressures, and connected for pressurized fluid communication witn the fluid conveyance system through the multi-valve arrangement prior to the first and second chromatographic columns and loaded or backflushed independently1 and (h) a multi-position multi-modal valve connecting or disconnecting the guard column with the fluid conveyance system through the fluid conduit assembly through which one port of the valve is connected to receive under pressure fluid mobile phase with or without multicomponent sample and through which another port is connected to deliver the same matarial received by the valve to the guard column and through which another port is connected to receive the mobile phase without sample or with multi-component sample having some components eluting from the column at different intervals, and through which another port of the valve delivers the same material received from the guard column to a port in one of the valves of the first multi-valve arrangement; and (i) a multi-position, multi-modal valve in the second multi-valve arrangement to isolate the detector from the superatmospheric pressure of the apparatus, and (j) at least one pump for supplying at least one mobile phase to the ingress-egress valve and the dual column chromatographic apparatus; and (k) at least one collection device to receive material from the dual chromatographic column system; and.

(l) a sample injector before the ingress-egress valve; and (m) a plurality of mobile phase reservoirs and a mixing chamber to provide for gradient elution in the chromatographic system.

27. The apparatus of claim 26, wherein the actuators are electronic actuators and which includes a microprocessor programmable controller for the actuators.

28. A method of separating overlapping peaks of a sample by chromatographic analysis on a dual chromatographic column system with column switching capability, comprising;

(a) equilibrating the precolumn and two chromatographic columns, (b) passing the mobile phase and sample through a precolumn to separate any particulate material, c) passing the mobile phase and sample through a first column having a stationary phase to separate the components of interest having overlapping peaks, transfer the sample with the components having two peaks of interest through a second column, backflush the first column, reequilibrate the first column with the mobile phase, elute the materials of interest from the second column, collect a small fraction of the first component from the second column, pass the eluant from the second column to a detector and to the first column, collect the trailing fraction of material from the second column as the last material elutes from the second column, backflush the second column, reequilibrate the second column, elute the materials of interest through both the first and second column, collect the separated product bearing fractions, backflush the first and second columns and any guard column.

* * * * *